US012800590B2

(12) United States Patent
Kaneko

(10) Patent No.: US 12,800,590 B2
(45) Date of Patent: Nov. 17, 2026

(54) ANALYSIS METHOD

(71) Applicant: SHIMADZU CORPORATION, Kyoto (JP)

(72) Inventor: Naoki Kaneko, Kyoto (JP)

(73) Assignee: SHIMADZU CORPORATION, Kyoto (JP)

( * ) Notice: Subject to any disclaimer, the term of this patent is extended or adjusted under 35 U.S.C. 154(b) by 637 days.

(21) Appl. No.: 18/266,977

(22) PCT Filed: Dec. 1, 2021

(86) PCT No.: PCT/JP2021/044101
§ 371 (c)(1),
(2) Date: Jun. 13, 2023

(87) PCT Pub. No.: WO2022/168417
PCT Pub. Date: Aug. 11, 2022

(65) Prior Publication Data

US 2024/0053357 A1 Feb. 15, 2024

(30) Foreign Application Priority Data

Feb. 8, 2021 (JP) ................................ 2021-018303

(51) Int. Cl.
*G01N 33/68* (2006.01)
*G01N 33/543* (2006.01)

(52) U.S. Cl.
CPC ....... *G01N 33/6848* (2013.01); *G01N 33/543* (2013.01); *G01N 33/6896* (2013.01); *G01N 2333/4709* (2013.01)

(58) Field of Classification Search
CPC ............. G01N 33/6848; G01N 33/543; G01N 33/6896; G01N 2333/4709; G01N 33/6851
See application file for complete search history.

(56) References Cited

U.S. PATENT DOCUMENTS

2004/0023289 A1* 2/2004 Klein ............... G01N 33/54388 435/7.1
2016/0334420 A1 11/2016 Kaneko
2017/0016910 A1 1/2017 Kaneko

FOREIGN PATENT DOCUMENTS

CN 101963595 A 2/2011
JP 2017-20980 A 1/2017
(Continued)

OTHER PUBLICATIONS

Extended European Search Report dated Nov. 4, 2024 in Application No. 21924802.8.
(Continued)

*Primary Examiner* — Jennifer Wecker
*Assistant Examiner* — Tracy Ching-Tian Colena
(74) *Attorney, Agent, or Firm* — Sughrue Mion, PLLC

(57) ABSTRACT

An analysis method includes a humidity measurement step of measuring humidity; a binding step of bringing a sample containing an analyte into contact with a carrier to bind the analyte to the carrier; an elution step of bringing the carrier to which the analyte is bound into contact with an eluate containing a volatile organic solvent to elute the analyte into the eluate; a disposition step of disposing the eluate into which the analyte has been eluted on a measurement plate for mass spectrometry; and a detection step of detecting the analyte by mass spectrometry, in which in the elution step, a use amount of the eluate is determined according to the humidity.

15 Claims, 2 Drawing Sheets

Specification includes a Sequence Listing.

(56) References Cited

FOREIGN PATENT DOCUMENTS

| | | | | | |
|---|---|---|---|---|---|
| WO | WO-2009144560 | A1 | * | 12/2009 | .......... H01J 49/0431 |
| WO | 2015/111430 | A1 | | 7/2015 | |

OTHER PUBLICATIONS

Chinese Office Action dated Oct. 28, 2025, issued in Chinese application No. 202180089543.3.
Naoki Kaneko et al., "Novel plasma biomarker surrogating cerebral amyloid deposition", Proc. Jpn. Acad., Ser. B Phys Biol Sci. 2014, pp. 353-364, vol. 90, No. 9.
Akinori Nakamura et al., "High performance plasma amyloid-β biomarkers for Alzheimer's disease", Nature, 2018, pp. 249-254, 554(7691).
Written Opinion for PCT/JP2021/044101, dated Jan. 18, 2022.
International Search Report for PCT/JP2021/044101, dated Jan. 18, 2022.
Communication dated Apr. 17, 2026, in Chinese Application No. 202180089543.3.

* cited by examiner

SEQUENCE LISTING

<160> NUMBER OF SEQ ID NOS: 8

<210> SEQ ID NO 1
<211> LENGTH: 37
<212> TYPE: PRT
<213> ORGANISM: Homo Sapiens

<400> SEQUENCE: 1

Asp Ala Glu Phe Arg His Asp Ser Gly Tyr Glu Val His His Gln Lys
1 5 10 15

Leu Val Phe Phe Ala Glu Asp Val Gly Ser Asn Lys Gly Ala Ile Ile
20 25 30

Gly Leu Met Val Gly
35

<210> SEQ ID NO 2
<211> LENGTH: 38
<212> TYPE: PRT
<213> ORGANISM: Homo Sapiens

<400> SEQUENCE: 2

Asp Ala Glu Phe Arg His Asp Ser Gly Tyr Glu Val His His Gln Lys
1 5 10 15

Leu Val Phe Phe Ala Glu Asp Val Gly Ser Asn Lys Gly Ala Ile Ile
20 25 30

Gly Leu Met Val Gly Gly
35

<210> SEQ ID NO 3
<211> LENGTH: 38
<212> TYPE: PRT
<213> ORGANISM: Homo Sapiens

<400> SEQUENCE: 3

Glu Phe Arg His Asp Ser Gly Tyr Glu Val His His Gln Lys Leu Val
1 5 10 15

Phe Phe Ala Glu Asp Val Gly Ser Asn Lys Gly Ala Ile Ile Gly Leu
20 25 30

Met Val Gly Gly Val Val
35

<210> SEQ ID NO 4
<211> LENGTH: 39
<212> TYPE: PRT
<213> ORGANISM: Homo Sapiens

<400> SEQUENCE: 4

Asp Ala Glu Phe Arg His Asp Ser Gly Tyr Glu Val His His Gln Lys
1 5 10 15

Leu Val Phe Phe Ala Glu Asp Val Gly Ser Asn Lys Gly Ala Ile Ile
20 25 30

Gly Leu Met Val Gly Gly Val
35

<210> SEQ ID NO 5
<211> LENGTH: 40
<212> TYPE: PRT
<213> ORGANISM: Homo Sapiens

<400> SEQUENCE: 5

Asp Ala Glu Phe Arg His Asp Ser Gly Tyr Glu Val His His Gln Lys

-continued

```
1               5                   10                  15

Leu Val Phe Phe Ala Glu Asp Val Gly Ser Asn Lys Gly Ala Ile Ile
            20                  25                  30

Gly Leu Met Val Gly Gly Val Val
        35                  40


<210> SEQ ID NO 6
<211> LENGTH: 40
<212> TYPE: PRT
<213> ORGANISM: Homo Sapiens

<400> SEQUENCE: 6

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val Val
        35                  40


<210> SEQ ID NO 7
<211> LENGTH: 42
<212> TYPE: PRT
<213> ORGANISM: Homo Sapiens

<400> SEQUENCE: 7

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val Val Ile Ala
        35                  40


<210> SEQ ID NO 8
<211> LENGTH: 43
<212> TYPE: PRT
<213> ORGANISM: Homo Sapiens

<400> SEQUENCE: 8

Val Lys Met Asp Ala Glu Phe Arg His Asp Ser Gly Tyr Glu Val His
1               5                   10                  15

His Gln Lys Leu Val Phe Phe Ala Glu Asp Val Gly Ser Asn Lys Gly
            20                  25                  30

Ala Ile Ile Gly Leu Met Val Gly Gly Val Val
        35                  40
```

ANALYSIS METHOD

CROSS REFERENCE TO RELATED APPLICATIONS

This application is a National Stage of International Application No. PCT/JP2021/044101 filed Dec. 1, 2021, claiming priority based on Japanese Patent Application No. 2021-018303 filed Feb. 8, 2021.

CORPORATION BY REFERENCE OF SEQUENCE LISTING

The content of the electronically submitted sequence listing, file name: Q286904_sequence listing as filed. TXT; size: 3,534 bytes; and date of creation: Jun. 12, 2023, filed herewith, is incorporated herein by reference in its entirety.

TECHNICAL FIELD

The present invention relates to an analysis method.

BACKGROUND ART

In the development of Alzheimer's disease, Aß-related peptides such as amyloid ß (Aß) generated by cleavage of amyloid precursor protein (APP) are deeply involved. Then, it has been reported that a plurality of Aß-related peptides in blood are detected by combining immunoprecipitation and mass spectrometry, and the detected specific Aß-related peptide ratio is promising as a blood biomarker of amyloid accumulation in the brain (Non-Patent Document 1 and Non-Patent Document 2).

As a method for measuring an Aß-related peptide in a blood sample, for example, a method including a step of binding an antibody-immobilizing carrier to a peptide in the sample, a step of washing these conjugates, a step of dissociating the peptide from the antibody-immobilizing carrier using an organic solvent-containing acidic aqueous solution, and a step of detecting the dissociated peptide by mass spectrometry is disclosed (Patent Document 1 and Patent Document 2). In the measurement methods of Patent Document 1 and Patent Document 2, a peptide can be detected even when a small amount of the peptide is present in the sample.

PRIOR ART DOCUMENTS

Patent Documents

Patent Document 1: WO 2015/111430 A
Patent Document 2: JP 2017-20980 A

Non-Patent Documents

Non-Patent Document 1: Kaneko N, Nakamura A, Washimi Y Kato T, Sakurai T, Arahata Y, Bundo M, Takeda A, Niida S, Ito K, Toba K, Tanaka K, Yanagisawa K.: Novel plasma biomarker surrogating cerebral amyloid deposition. Proc Jpn Acad Ser B Phys Biol Sci. 2014; 90(9): 353-364.

Non-Patent Document 2: Nakamura A, Kaneko N, Villemagne V L, Kato T, Doecke J, Dore V, Fowler C, Li Q X, Martins R, Rowe C, Tomita T, Matsuzaki K, Ishii K, Ishii K, Arahata Y, Iwamoto S, Ito K, Tanaka K, Masters C L, Yanagisawa K.: High performance plasma amyloid-ß biomarkers for Alzheimer's disease. Nature. 2018; 554 (7691): 249-254.

SUMMARY OF THE INVENTION

Problems to be Solved by the Invention

Incidentally, when an eluate in which only the analyte is eluted by removing contaminants by immunoprecipitation is measured by mass spectrometry, the higher the concentration (degree of concentration) of the analyte in the eluate, that is, the smaller the use amount of the elution solution, the stronger the signal intensity of the analyte detected by mass spectrometry, so that highly sensitive analysis is possible. On the other hand, from the viewpoint of analysis accuracy, it is desirable that the number of samples to be subjected to the mass spectrometry, that is, the number of mass spectrometry results (mass spectra) is plural.

Therefore, it is attempted to elute the analyte with a small amount of eluate so as to have a high concentration, divide the small amount of eluate into a plurality of samples, and dispose the samples on a measurement plate for mass spectrometry. However, when such measurement is performed a plurality of times while changing the environment such as date and place, the amount of the eluate is insufficient, and the amount becomes smaller than the desired number of sample results (mass spectra) in some cases, and the number of data is reduced, leading to a problem that the accuracy is lowered. On the other hand, if the amount of the eluate is increased to create an excessive margin in order to avoid the above problem, a problem that elution cannot be performed at a high concentration and analysis cannot be performed with high sensitivity occurs.

An object of the present invention is to detect an analyte with high sensitivity and high accuracy at the time of analysis using mass spectrometry.

Means for Solving the Problems

An analysis method according to a first aspect of the present invention includes: a humidity measurement step of measuring humidity; a binding step of bringing a sample containing an analyte into contact with a carrier to bind the analyte to the carrier; an elution step of bringing an eluate containing a volatile organic solvent into contact with the carrier to which the analyte is bound to elute the analyte into the eluate; a disposition step of disposing the eluate into which the analyte has been eluted on a measurement plate for mass spectrometry; and a detection step of detecting the analyte by mass spectrometry. In the elution step, the use amount of the eluate is determined according to the humidity.

Effects of the Invention

According to the first aspect of the present invention, an analyte can be detected with high sensitivity and high accuracy.

MODE FOR CARRYING OUT THE INVENTION

1. First Aspect

Figure 1:
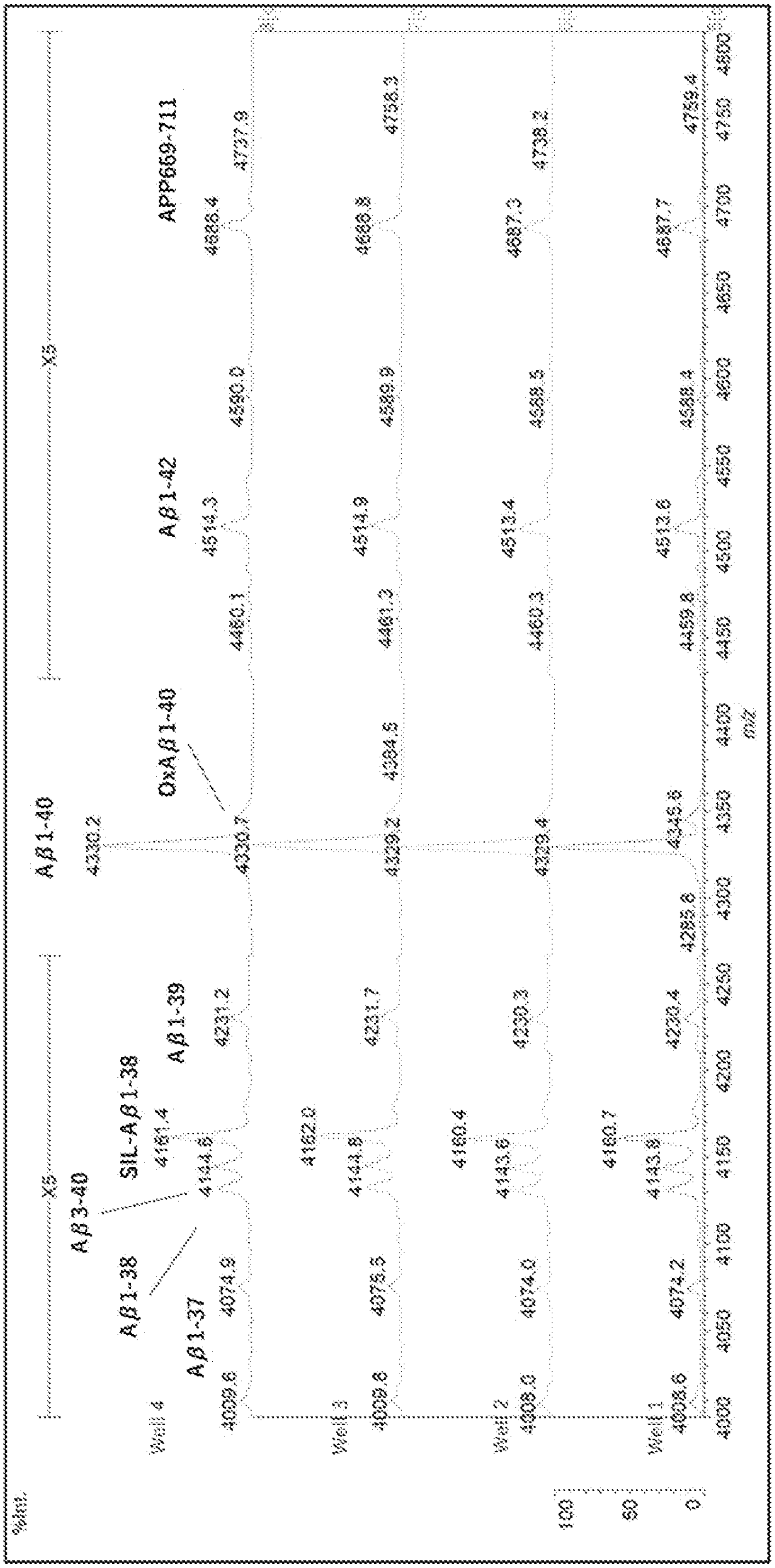
FIG. 1 shows a mass spectrum of an Aß-related peptide detected by MALDI-TOF/MS apparatus under a first environment (humidity: 58.0%).

As an analysis method of the first aspect of the present invention, an analysis method when a polypeptide is adopted as an analyte, a biological sample is adopted as a sample, and MALDI (Matrix Assisted Laser Desorption/Ionization) is adopted as mass spectrometry is described.

The analysis method of the first aspect includes a humidity measurement step, a first binding step (an example of the "binding step" of the present invention), a first washing step, a first elution step, a neutralization step, a second binding step, a second washing step, a second elution step (an example of the "elution step" of the present invention), a disposition step, and a detection step.

The "polypeptide" to be analyzed and measured of the first aspect also includes "peptide" and "protein". Polypeptides include various ones, and specifically include Aß-related peptides. The Aß-related peptide is AB generated by cleavage of amyloid precursor protein (APP), and a peptide containing even a part of the sequence of Aß. In particular, it is shown in the examples and also disclosed in WO 2015/178398 A.

(Humidity Measurement Step)

In the humidity measurement step, humidity is measured. Specifically, humidity in an analysis space (chamber) in which the second elution step and the disposition step described later are performed is measured. Generally, these are performed in the same space, but when they are different, humidity in each space is measured, and the average humidity obtained by proportionally dividing the time from immediately after the start of the second elution step until the eluate is disposed on the measurement plate may be used.

(First Binding Step)

In the first binding step, the biological sample is brought into contact with a first carrier (an example of the "carrier" of the present invention). For example, the biological sample is mixed with the first carrier. As a result, the polypeptide is bound to the first carrier to obtain a first conjugate.

Examples of the biological sample include body fluids such as blood, cerebrospinal fluid, urine, body secretion, saliva, and sputum; feces; and the like. The blood sample includes whole blood, plasma, serum, and the like. The blood sample may be obtained by subjecting whole blood collected from an individual to treatment such as centrifugation and cryopreservation.

The biological sample is usually brought into contact with the first carrier in a state of being mixed with the binding solution.

As the binding solution, a binding solution used in a normal immunoprecipitation can be used. Preferably, the binding solution includes a neutral buffer containing a surfactant. By containing a surfactant, non-specific adsorption can be suppressed.

The surfactant is preferably a neutral surfactant from the viewpoint of suppression of protein denaturation, ease of removal, and the like. Examples of the neutral surfactant include surfactants having maltose in the hydrophilic moiety, such as n-decyl-ß-D-maltoside (DM), n-dodecyl-ß-D-maltoside (DDM), and n-nonyl-ß-D-thiomaltoside (NTM); surfactants having trehalose in the hydrophilic moiety, such as α-D-glucopyranosyl α-D-glucopyranoside monooctanoate (trehalose C8), α-D-glucopyranosyl α-D-glucopyranoside monododecanoate (trehalose C12), and α-D-glucopyranosyl α-D-glucopyranoside monomyristate (trehalose C14); surfactants having glucose in the hydrophilic moiety, such as n-octyl-ß-D-thioglucoside, n-octyl-ß-D-glucoside, and n-heptyl-ß-D-thioglucoside; and the like. These can be used alone or in combination of two or more.

Examples of the buffer include a Tris buffer, a phosphate buffer, a HEPES buffer, an ammonium acetate buffer, and the like. The pH of the buffer is, for example, 6.5 or more and 8.5 or less.

The surfactant concentration in the binding solution is, for example, 0.001% (w/v) or more, preferably 0.05% (w/v) or more, and is, for example, 10% (w/v) or less, and preferably 2% (w/v) or less.

The first carrier may be any carrier to which the polypeptide can bind, and examples thereof include an antibody-immobilizing carrier.

The antibody immobilized on the first carrier may have an antigen binding site capable of recognizing a polypeptide, and examples thereof include immunoglobulins or fragments thereof having an antigen binding site capable of recognizing a polypeptide.

Examples of the immunoglobulin include IgG (IgG1, IgG2, IgG3, IgG4), IgM, IgA, IgY, IgD, IgE, and the like. The immunoglobulin is appropriately determined according to the analyte, and a known immunoglobulin may be adopted. Examples of the immunoglobulin fragment include F(ab')2, F(ab'), F(ab), Fd, Fv, L chain, H chain, and the like. When the analyte is an Aß-related peptide, the immunoglobulin or a fragment thereof (anti-Aß-related peptide antibody) having an antigen binding site capable of recognizing the Aß-related peptide is, for example, 6E10, 4G8, 1E11, 11A50-B10, 12F4, 9C4, 82E1, 12B2, 1A10, a fragment thereof, or the like. The antibody may be either a monoclonal antibody or a polyclonal antibody.

Examples of the material of the first carrier include agarose, sepharose, dextran, silica gel, polyacrylamide, polystyrene, polyethylene, polypropylene, polyester, polyacrylonitrile, a (meth)acrylic acid-based polymer, a fluororesin, a metal complex resin, glass, metal, a magnetic body, and the like. In the first elution step and the second elution step described later, a magnetic body is preferable from the viewpoint that only the carrier can be easily extracted by magnetic force and the decrease in the eluate can be suppressed when the carrier is taken out.

The shape of the first carrier may be any shape such as a spherical shape (including a bead shape), a plate shape, a needle shape, and an irregular shape, and may be a flow path wall in a microdevice or the like.

Before the first binding step, pretreatment for removing antibodies such as IgG and IgM may be performed as necessary.

(First Washing Step)

In the first washing step, after the first binding step, the first conjugate is washed using a washing liquid.

As a washing method, a known method may be adopted, and washing is preferably performed a plurality of times. For example, washing is performed using a neutral buffer containing a surfactant, followed by washing using a neutral buffer not containing a surfactant.

As the neutral buffer containing a surfactant, those similar to the surfactant and neutral buffer exemplified in the binding solution can be used. As a result, for example, unnecessary components (such as blood proteins, lipids, and glycolipids) having high hydrophobicity can be effectively removed.

As a neutral buffer containing no surfactant, a neutral buffer similar to the neutral buffer exemplified in the binding solution can be used. This makes it possible to suppress foaming caused by the surfactant remaining in the first conjugate.

As the washing method, a general method may be adopted, and examples thereof include a method of stirring a carrier in a washing liquid, a method of spraying a washing liquid from a washing nozzle, and the like.

After washing with these neutral buffers, washing with water may be further performed as necessary.

(First Elution Step)

In the first elution step, after the first washing step, the first conjugate is brought into contact with the first eluate. As a result, the polypeptide is dissociated from the first conjugate, and the polypeptide is eluted into the first eluate.

The first eluate is a liquid for eluting the polypeptide, and for example, an acidic aqueous solution such as a glycine buffer or hydrochloric acid is used. The pH of the first elution solution is, for example, 1.0 or more and 3.5 or less.

The first eluate preferably contains a surfactant. This makes it possible to more reliably dissociate the polypeptide from the first conjugate. In addition, adhesion of the eluted polypeptide to a container such as a test tube or a microplate is suppressed. Therefore, the recovery rate of the polypeptide can be reliably improved.

Examples of the surfactant include the same surfactants as those exemplified in the binding solution. The surfactant concentration in the first eluate is, for example, 0.001% (w/v) or more, preferably 0.05% (w/v) or more, and is, for example, 10% (w/v) or less, and preferably 2% (w/v) or less.

(Neutralization Step)

In the neutralization step, after the first elution step, the first eluate from which the polypeptide has been eluted is neutralized. Thereby, a purified solution containing the polypeptide is obtained.

As a neutralization method, for example, the first eluate is mixed with a neutral buffer. Preferably, the first eluate is mixed with a neutral buffer containing a surfactant.

Examples of the neutral buffer and the surfactant include those similar to the neutral buffer and the surfactant exemplified in the binding solution.

The pH of the purified solution is, for example, pH of 6.0 or more, and preferably 6.5 or more, and is, for example, 8.5 or less, and preferably 8.0 or less. Accordingly, in the second binding step, the bonding efficiency can be improved.

(Second Binding Step)

In the second binding step, the purified solution is brought into contact with the second carrier after the neutralization step. As a result, the polypeptide is bound to the second carrier to obtain a second conjugate.

The second carrier is preferably an antibody-immobilizing carrier, and specific examples thereof include the same antibody-immobilizing carriers as exemplified for the first carrier.

(Second Washing Step)

In the second washing step, after the second binding step, the second conjugate is washed using a washing liquid. As the washing method, a known method may be adopted, and specifically, a method similar to the washing method exemplified in the first washing step may be performed.

(Second Elution Step)

In the second elution step, after the second washing step, the second conjugate is brought into contact with the second eluate. As a result, the polypeptide is dissociated from the second conjugate, and the polypeptide is eluted into the second eluate.

The second eluate is a liquid for eluting the polypeptide, and for example, an acidic aqueous solution such as a glycine buffer or hydrochloric acid is used. The pH of the second elution solution is, for example, 1.0 or more and 3.5 or less.

The second eluate contains a volatile organic solvent. As a result, the polypeptide can be efficiently dissociated from the second conjugate and eluted in the second eluate, and the recovery rate of the polypeptide can be improved.

Examples of such a volatile organic solvent include an organic solvent miscible with water at an arbitrary ratio, and include acetonitrile, methanol, ethanol, acetone, toluene, isopropanol, hexane, butanol, cyclohexane, ethylene glycol, benzene, chloroform, acetaldehyde, triethylamine, phenol, naphthalene, formaldehyde, tetrahydrofuran, ethyl acetate, and the like, and preferably include acetonitrile, methanol, ethanol, acetone, isopropanol, and the like. These may be used alone or in combination of two or more.

The concentration of the volatile organic solvent in the second eluate is, for example, 10% (v/v) or more, preferably 30% (v/v) or more, and more preferably 55% (v/v) or more, and is, for example, 90% (v/v) or less, preferably 85% (v/v) or less, and more preferably 80% (v/v) or less. By setting the concentration in the above range, the dissociation of the polypeptide from the second carrier efficiently occurs, and sensitivity (S/N ratio) at the time of mass spectrometry can be improved.

The second eluate preferably contains an amino acid such as methionine. As a result, it is possible to reduce oxidation of the polypeptide and to improve analysis accuracy before the polypeptide is disposed on the measurement plate for mass spectrometry and analysis is started. The amino acid concentration in the second eluate is, for example, 0.01 mM or more, and preferably 0.05 mM or more, and is, for example, 5 mM or less, and preferably 1 mM or less.

In this step, the use amount of the second eluate to be brought into contact with the second conjugate is determined according to the humidity. That is, the use amount of the eluate when the humidity is low is determined so as to be larger than the use amount of the eluate when the humidity is high.

Specifically, first, the use amount (first use amount) of the second eluate under a first environment (first humidity) is determined. That is, the humidity (first humidity) is measured under the first environment. Then, at the first humidity, the second eluate is determined without excess or deficiency so that the desired number of samples (desired number of wells) and a desired amount of samples can be disposed on the MALDI plate. At this time, the amount of the second eluate is reduced as much as possible in order to increase the polypeptide concentration. If necessary, a dead amount remaining in the test tube or the tube and a volatile content of the volatile organic solvent are also added. As an example, when the second eluate sample to be disposed in each well is set to 1 μL and the number of samples (number of wells) is set to four, the total is 4 μL, but a dead volume (for example, 2 μL) and a volatilization amount (for example, 2 μL) are also added thereto. Next, the humidity is measured under the second environment (second humidity), and the use amount (second use amount) of the second eluate is determined based on the first use amount at the first humidity according to the humidity. That is, the humidity (second humidity) is measured under the second environment. Then, when the second humidity is lower than the first humidity, the second use amount is determined to be larger than the first use amount. On the other hand, when the second humidity is higher than the first humidity, the second use amount is determined to be smaller than the first use amount.

The calculation method for determining the second use amount is appropriately determined according to the organic solvent type, the humidity, and the disposition time. For example, when the difference between the first humidity and the second humidity is 20% or more (preferably 30% or more), the ratio between the first use amount and the second use amount may be, for example, 1.1 or more (for example, 1.5 or less). As an example, when the first humidity is 50% or more, the first use amount is 8 μL, and the second humidity is 30% or less, the second use amount may be about 9 μL.

The temperature conditions in the first environment and the second environment are not limited, and may be the same or different, but are preferably substantially the same temperature, specifically, the temperature difference between the first environment and the second environment is 10 degrees or less.

The determination of the use amount in the second elution step is particularly effective when, in the analysis step, a desired time, for example, 3 minutes or more, preferably 5 minutes or more, and for example, 60 minutes or less, preferably 30 minutes or less is required from the start of the second elution step to the completion of the disposition step. It is also effective when the concentration of the volatile organic solvent in the second eluate is high, for example, 10% (v/v) or more, and preferably 55% (v/v) % or more.

The first aspect of the present invention has been made based on the following knowledge, but the scope of the present invention is not limited to the following knowledge. The second eluate into which the polypeptide has been eluted is measured by MALDI described later, and the polypeptide is detected. At this time, as the amount of the eluate to be subjected to MALDI is smaller, that is, as the concentration of the polypeptide is higher, the detection result is obtained with higher sensitivity, and thus it is preferable that the amount of the eluate is small. In addition, in order to enhance detection accuracy, the number of samples analyzed by MALDI (the number of wells used) is preferably plural or more. Therefore, the use amount of the second eluate contributes to the sensitivity and accuracy of the analysis.

Then, when the polypeptide is eluted in a low amount of the second eluate at a high concentration, disposed in a plurality of wells (desired number of samples), and MALDI measurement is performed a plurality of times, for example, when measurement is performed a plurality of times over different dates and times, results of the number of samples smaller than the desired number of samples are obtained, and the accuracy may be deteriorated. As a result of intensive studies on this phenomenon, the present inventor has focused on the measurement environment, and have found that when the measurement environment is low humidity, the volatile organic solvent of the second eluate volatilizes before the analyte starts to be eluted into the second eluate and is to be disposed on the measurement plate for MALDI apparatus, so that the liquid amount of the second eluate is insufficient, and the second eluate cannot be disposed on the MALDI plate.

Then, by measuring the humidity and determining the use amount of the second eluate according to the measured humidity, the polypeptide was eluted into the eluate at a high concentration, and shortage of the liquid amount (as a result, the number of samples) of the second eluate disposed on the MADLI plate was prevented. As a result, MALDI analysis could be performed using a high concentration and a desired number of samples, and high sensitivity and high accuracy analysis were enabled.

(Disposition Step)

In the disposition step, after the second elution step, the second eluate is disposed on the measurement plate. Specifically, the second eluate into which the polypeptide has been eluted is distributed to each well of a MALDI plate for MALDI apparatus.

The number of wells (the number of measurement samples) in which the second eluate is distributed to the MALDI plate is preferably plural or more, specifically 2 wells or more, and preferably 4 wells or more, and for example, 50 wells or less, preferably 20 wells or less, and more preferably 10 wells or less. When the number of wells is plural, the number of measurement samples (the number of mass spectra to be measured) increases, and the detection accuracy can be improved.

The amount of the second eluate disposed in each well is, for example, 0.2 μL or more, and preferably 0.5 lit or more, and is, for example, 4 μL or less, and preferably 2 μL or less. When the amount per well unit is the above lower limit or more, the substance to be analyzed can be reliably detected. In addition, when the amount per well unit is the above upper limit or less, the number of samples of the analyte to be subjected to measurement can be increased.

This operation may be performed using an automatic dispensing device, or manually using a pipette or the like.

Note that a matrix may be disposed on the MALDI plate in advance before disposing the second eluate. Conversely, after the second eluate is disposed on the MALDI plate, the matrix may be disposed on the second solution. The matrix will be described later in the analysis step.

(Analysis Step)

In the analysis step, after the disposition step, the polypeptide contained in the second eluate is detected by MALDI.

For detection by MALDI, for example, MALDI-TOF (Matrix-Assisted Laser Desorption/Ionization-Time of Flight) type mass spectrometer, MALDI-IT (Matrix-Assisted Laser Desorption/Ionization-Ion Trap) type mass spectrometer, MALDI-IT-TOF (Matrix-Assisted Laser Desorption/Ionization-Ion Trap-Time of Flight) type mass spectrometer, MALDI-FTICR (Matrix-Assisted Laser Desorption/Ionization-Fourier Transform Ion Cyclotron Resonance) type mass spectrometer, or the like may be used and operated according to a conventional method.

The matrix is disposed, for example, by dropping a matrix-containing solution into the MALDI plate and drying the solution.

Examples of the matrix include α-cyano-4-hydroxycinnamic acid (CHCA), 2,5-dihydroxybenzoic acid, sinapinic acid, 3-aminoquinoline, and the like. These can be used alone or in combination of two or more.

Examples of the solvent contained in the matrix include acetonitrile, trifluoroacetic acid, methanol, ethanol, water, and the like. These can be used alone or in combination of two or more.

The matrix concentration in the matrix-containing solvent is, for example, 0.1 mg/mL or more, and preferably 0.5 mg/mL or more, and is, for example, 50 mg/mL or less, and preferably 10 mg/mL or less.

Preferably, a matrix additive is used in combination with the matrix. Examples of the matrix additive include a phosphonic acid group-containing compound, an ammonium salt, and the like, and preferably include a phosphonic acid group-containing compound from the viewpoint that an adverse effect on the background due to the remaining of the washing liquid can be suppressed. Examples of the phosphonic acid group-containing compound include phosphonic acid, methylphosphonic acid, phenylphosphonic acid, 1-naphthylmethylphosphonic acid, methylenediphosphonic acid (MDPNA), ethylene diphosphonic acid, ethane-1-hydroxy-1, 1-diphosphonic acid, nitrilotriphosphonic acid, ethylene diaminotetraphosphonic acid, and the like.

The matrix additive concentration in the matrix-containing solvent is, for example, 0.01% (w/v) or more, and preferably 0.1% (w/v) or more, and is, for example, 10% (w/v) or less, and preferably 1% (w/v) or less.

2. Other Aspects (1) In the analysis method of the first aspect, two immunoprecipitations (affinity purification) are performed, but for example, one immunoprecipitation may be performed. In this case, the analysis method includes a humidity measurement step, a first binding step (binding step), a first washing step (washing step), a second elution step (elution step), a disposition step, and a detection step. The first aspect is preferable from the viewpoint that the polypeptide can be analyzed even when the abundance of the polypeptide in the biological sample is even smaller.

(2) In the analysis method of the first aspect, the humidity measurement step is first performed, but the humidity measurement step is not limited as long as it is before the second elution step, and may be performed, for example, after the first binding step, the first washing step, or the first neutralization step.

(3) In the analysis method of the first aspect, the immunoprecipitation is performed using an antibody-immobilizing carrier as an antibody, but the method is not limited to the immunoprecipitation, and for example, a solid-phase extraction method can also be performed. In this case, the solid-phase extraction method preferably adopts a reversed-phase retention mode. The carrier is a carrier having a functional group on the surface, and examples of the functional group include an octyl group (C8), an octadecyl group (C18), a benzene ring, and the like.

(4) In the analysis method of the first aspect, a biological sample is used as a sample, and an analyte is set to a polypeptide, but is not limited thereto. The sample may be, for example, a biological sample (cell culture supernatant, cell lysate, microorganism culture supernatant, microorganism lysate, or the like), a food or beverage, contaminated water, soil, or the like. Also, a digested peptide produced by digesting the polypeptide contained in the sample with a protease (trypsin, Lys-C, Lys-N, Glu-C, thermolysin, AspN, chymotrypsin, or the like) may also be used as the sample. The substance to be analyzed may be, for example, a biological component other than the polypeptide, a pharmaceutical component, a food component, a residual agrochemical component, or the like.

(5) In the analysis method of the first aspect, MALDI is adopted as ionization of mass spectrometry, but for example, ionization other than MALDI, specifically, LDI (laser desorption ionization), SELDI (surface enhanced laser desorption ionization), PALDI (nanoparticle-assisted laser desorption ionization), or the like may be adopted.

3. Aspects

It is understood by those skilled in the art that the plurality of exemplary embodiments described above are specific examples of the following aspects.

(Item 1) An analysis method according to one aspect may include a humidity measurement step of measuring humidity; a binding step of bringing a sample containing an analyte into contact with a carrier to bind the analyte to the carrier; an elution step of bringing the carrier to which the analyte is bound into contact with an eluate containing a volatile organic solvent to elute the analyte into the eluate; a disposition step of disposing the eluate into which the analyte has been eluted on a measurement plate for mass spectrometry; and a detection step of detecting the analyte by mass spectrometry, and in the elution step, a use amount of the eluate may be determined according to the humidity.

According to the analysis method of item 1, the analyte can be analyzed with high sensitivity and high accuracy by mass spectrometry even under different environments.

(Item 2) In the analysis method according to item 1, in the elution step, the use amount of the eluate when the humidity is low may be determined so as to be larger than the use amount of the eluate when the humidity is high.

According to the analysis method of item 2, the analyte can be analyzed with high sensitivity and high accuracy by mass spectrometry even in an environment with low humidity (Item 3) In the analysis method according to item 1 or 2, in the disposition step, the eluate may be disposed in a plurality of wells of the measurement plate.

According to the analysis method of item 3, since a plurality of mass spectrometry results can be obtained from one sample, analysis can be performed with high accuracy.

(Item 4) In the analysis method according to any one of items 1 to 3, the volatile organic solvent may contain at least one selected from the group consisting of acetonitrile, methanol, ethanol, acetone, toluene, isopropanol, hexane, butanol, cyclohexane, ethylene glycol, benzene, chloroform, acetaldehyde, triethylamine, phenol, naphthalene, formaldehyde, tetrahydrofuran, and ethyl acetate.

According to the analysis method of item 4, the substance to be measured can be efficiently eluted into the eluate, and the recovery rate of the substance to be measured subjected to mass spectrometry can be improved. As a result, the sensitivity of mass spectrometry can be improved.

(Item 5) In the analysis method according to any one of items 1 to 4, a concentration of the volatile organic solvent in the eluate may be 10% (v/v) or more.

According to the analysis method of item 5, the substance to be measured can be eluted into the eluate more efficiently, and the recovery rate of the substance to be measured subjected to mass spectrometry can be more reliably improved. As a result, the sensitivity of mass spectrometry can be more reliably improved.

(Item 6) In the analysis method according to any one of items 1 to 5, the mass spectrometry may be matrix-assisted laser desorption/ionization.

According to the analysis method of item 6, analysis of a biopolymer such as a polypeptide can be facilitated.

(Item 7) In the analysis method according to any one of items 1 to 6, the analyte may be a polypeptide, and the carrier may be an antibody-immobilizing carrier.

According to the analysis method of item 7, a polypeptide such as an Aß-related peptide can be detected.

(Item 8) In the analysis method according to item 7, the antibody immobilized on the antibody-immobilizing carrier may be an anti-Aß-related peptide antibody, and the analyte may be an Aß-related peptide.

According to the analysis method of item 8, the onset of Alzheimer's dementia and the like can be examined.

EXAMPLES

Next, the present invention will be described in detail with reference to Examples and Comparative Examples, but the scope of the present invention is not limited thereto.

(Preparation of Antibody Beads)

Clone 6E10 (Covance corporation) of an anti-AB antibody (IgG) having 3-8 residues of amyloid ß protein (Aß) as an epitope was prepared. About $3.3\times10^8$ magnetic beads (Dynabeads M-270 Epoxy) with respect to 100 µg of an anti-AB antibody (IgG) were reacted in an immobilization buffer (a 0.1 M phosphate buffer containing 1.3 M ammonium sulfate; pH 7.4) at 37° C. for 16 to 24 hours. Thus, antibody beads as an antibody-immobilizing carrier were prepared.

Example 1

1. Measurement Under First Environment (Humidity Measurement Step)

The humidity in the room was measured and found to be 58.0%. The temperature was 23.1° C.

(First Binding Step, First Washing Step, First Elution Step)

The analyte was Aß-related peptide, and human plasma was prepared. 250 µL of human plasma was mixed with 250 µL of a neutral buffer (0.2% (w/v) DDM, 0.2% (w/v) NTM, 800 mM GlcNAc, 100 mM Tris-HCl, 300 mM NaCl; pH 7.4) containing 11 µM of stable isotope labeled Aß1-38 (SIL-Aß1-38), and the mixture was allowed to stand on ice for 5 to 60 minutes. The human plasma was mixed with antibody beads and shaken at 4° C. for 1 hour. SIL-Aß1-38 was used as an internal standard for standardizing the signal intensity of the mass spectrum. Thereafter, the antibody beads were washed once with 100 µL of a washing buffer (0.1% (w/v) DDM, 0.1% (w/v) NTM, 50 mM Tris-HCl, 150 mM NaCl; pH 7.4) and washed once with 50 µL of a 50 mM ammonium acetate buffer. The antibody beads were then added to a first eluate (50 mM glycine buffer with 0.1% (w/v) DDM; pH 2.8) to elute the Aß-related peptide into the first eluate.

(Neutralization Step)

The first eluate containing the Aß-related peptide was mixed with a neutral buffer (0.2% (w/v) DDM, 800 mM GlcNAc, 300 mM Tris-HCl, 300 mM NaCl; pH 7.4) to obtain a purified solution.

(Second Binding Step, Second Washing Step, Second Elution Step)

The purified solution was mixed with antibody beads and shaken at 4° C. for 1 hour. Thereafter, the antibody beads were washed twice with 50 µL of a washing buffer (0.1% (w/v) DDM, 50 mM Tris-HCl, 150 mM NaCl; pH 7.4), washed once with 50 µL of a 50 mM ammonium acetate buffer, and washed once with 30 µL of water. Thereafter, the antibody beads were brought into contact with 8 µL of a second eluate (70% (v/v) acetonitrile in water with 5 mM HCl and 0.1 mM methionine; pH 2.3) to elute the Aß-related peptide into the second eluate.

(Disposition Step)

AMALDI-TOF MS apparatus (manufactured by Shimadzu Corporation, AXIMA Performance) was used as a mass spectrometer. A 0.5 mg/mL CHCA/0.2% (w/v) MDPNA matrix solution was prepared using α-cyano-4-hydroxycinnamic acid (CHCA) as a matrix for Linear TOF, methylene diphosphonic acid (MDPNA) as a matrix additive, and acetonitrile as a solvent. 0.5 µL each of the matrix solution was added dropwise to 4 wells of a MALDI plate (p Focus MALDI plate 900 µm (Hudson Surface Technology, Inc., Fort Lee, NJ)), and dried. A second eluate containing an Aß-related peptide was added dropwise to these 4 wells and disposed. The time required from the start of the second elution step to the completion of the disposition step was 5 minutes and 15 seconds.

(Detection Step)

MALDI-TOF MS was operated to detect Aß-related peptides. As a setting condition, mass spectrum data was acquired by Linear TOF in a positive ion mode using AXIMA Performance (Shimadzu/KRATOS, Manchester, UK). 400 Spots and 16000 shots were accumulated for 1 well. The m/z value of Linear TOF was expressed as the peak average mass. The m/z value was calibrated using human angiotensin II, human ACTH fragment 18-39, bovine insulin oxidized beta-chain, and bovine insulin as external standards.

2. Measurement Under Second Environment (Humidity Measurement Step)

The humidity in the room was measured changing the date and time and found to be 21.2%. The temperature was 21.2° C.

(First Binding Step to Detection Step)

The same procedure as in the first environment was carried out except that the use amount of the second eluate was changed to 9 µL.

<Results>

Figure 2:
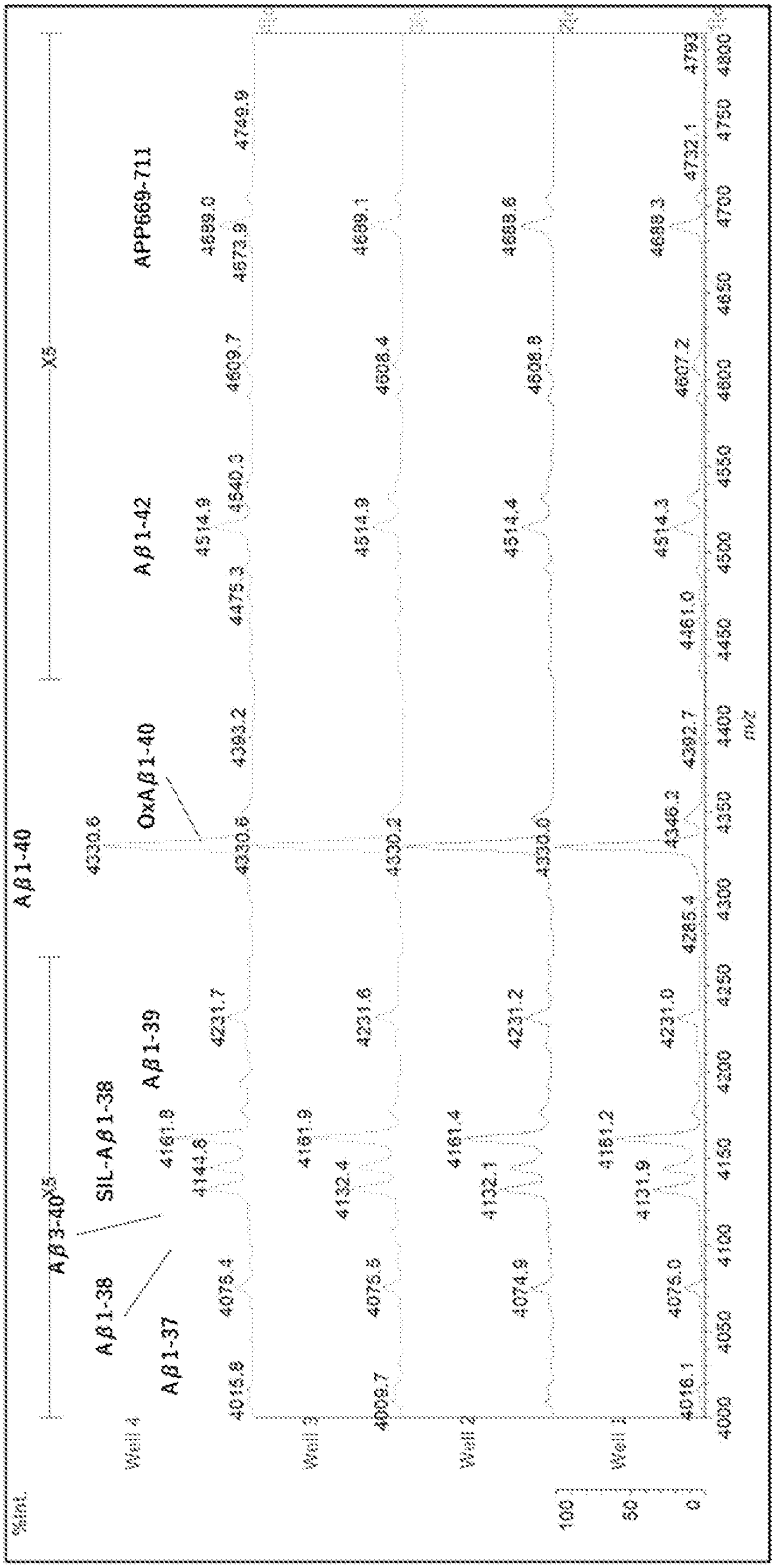
FIG. 2 shows a mass spectrum of an Aß-related peptide detected by MALDI-TOF/MS apparatus under a second environment (humidity 21.2%).

FIG. 1 shows a mass spectrum in the first environment (humidity 58.0%). FIG. 2 shows a mass spectrum in the second environment (humidity 21.2%). In FIGS. 1 and 2, the vertical axis represents signal intensity, and the horizontal axis represents mass-to-charge ratio (m/z). Table 1 shows amino acid sequences of the Aß-related peptides as the analyte. From FIGS. 1 and 2, it could be confirmed with high sensitivity that the Aß-related peptide was eluted in both environments of the high humidity condition and the low humidity condition. In addition, a mass spectrum of the desired number of samples (Wells 1 to 4) was obtained, and it could be confirmed that highly accurate detection was possible.

TABLE 1

| NO. | Name | Amino acid sequence |
|---|---|---|
| 1 | Aβ 1-37 | DAEFRHDSGYEVHHQKLVFFAE DVGSNKGAIIGLMVG |
| 2 | Aβ 1-38 | DAEFRHDSGYEVHHQKLVFFAE DVGSNKGAIIGLMVGG |
| 3 | Aβ 3-40 | EFRHDSGYEVHHQKLVFFAEDV GSNKGAIIGLMVGGVV |
| 4 | Aβ 1-39 | DAEFRHDSGYEVHHQKLVFFAE DVGSNKGAIIGLMVGGV |
| 5 | Aβ 1-40 | DAEFRHDSGYEVHHQKLVFFAE DVGSNKGAIIGLMVGGVV |
| 6 | OxAβ 1-40 | DAEFRHDSGYEVHHQKLVFFAE DVGSNKGAIIGL<u>M</u>VGGVV |
| 7 | Aβ 1-42 | DAEFRHDSGYEVHHQKLVFFAE DVGSNKGAIIGLMVGGVVIA |
| 8 | APP669-711 | VKMDAEFRHDSGYEVHHQKLVF FAEDVGSNKGAIIGLMVGGVV |

REFERENCE EXAMPLE

The same procedures were carried out in the same manner as in the second environment, except that the use amount of the second eluate was 8 µL as in the first environment. Then, the second eluate was disposed in only 3 wells in the MALDI plate, and the desired number of samples could not be analyzed.

The invention claimed is:

1. An analysis method comprising:

performing a first analysis under a first environment, the first analysis comprising:

a first humidity measurement step of measuring a first humidity;

a first-environment binding step of bringing a first sample containing an analyte into contact with a carrier for the first analysis to bind the analyte to the carrier for the first analysis;

and;

a first-environment elution step of bringing the carrier for the first analysis to which the analyte is bound into contact with an eluate for the first analysis containing a volatile organic solvent to elute the analyte into the eluate for the first analysis, wherein a first use amount is used for the eluate for the first analysis;

performing a second analysis under a second environment, the second analysis comprising:

a second humidity measurement step of measuring a second humidity;

a determination step of comparing the first humidity and the second humidity, and determining a second use amount based on the first use amount, wherein when a difference between the first humidity and the second humidity is 20% or more, a ratio of the second use amount to the first use amount is 1.1 or more;

a second-environment binding step of bringing a second sample containing the analyte into contact with a carrier for the second analysis to bind the analyte to the carrier for the second analysis; and a second-environment elution step of bringing the carrier for the second analysis to which the analyte is bound into contact with an eluate for the second analysis containing the volatile organic solvent to elute the analyte into the eluate for the second analysis to obtain a second-environment eluate, wherein the second use amount is used for the eluate for the second analysis;

a disposition step of disposing the second-environment eluate on a measurement plate for mass spectrometry; and a detection step of detecting the analyte contained in the second-environment eluate disposed on the measurement plate by mass spectrometry.

2. The analysis method according to claim 1, wherein in the disposition step, the second-environment eluate is disposed in a plurality of wells of the measurement plate.

3. The analysis method according to claim 1, wherein the volatile organic solvent contains at least one selected from the group consisting of acetonitrile, methanol, ethanol, acetone, toluene, isopropanol, hexane, butanol, cyclohexane, ethylene glycol, benzene, chloroform, acetaldehyde, triethylamine, phenol, naphthalene, formaldehyde, tetrahydrofuran, and ethyl acetate.

4. The analysis method according to claim 1, wherein a concentration of the volatile organic solvent in the eluate for the first analysis and the eluate for the second analysis is 10% (v/v) or more.

5. The analysis method according to claim 1, wherein the mass spectrometry is matrix-assisted laser desorption/ionization.

6. The analysis method according to claim 1, wherein the analyte is a polypeptide, and the carrier for the first analysis and the carrier for the second analysis are antibody-immobilizing carriers.

7. The analysis method according to claim 6, wherein the antibody immobilized on the antibody-immobilizing carriers is an anti-Aβ-related peptide antibody, and the analyte is an Aβ-related peptide.

8. The analysis method according to claim 1, wherein when the difference between the first humidity and the second humidity is 30% or more, the ratio of the second use amount to the first use amount is 1.5 or less.

9. The analysis method according to claim 1, wherein in the second humidity measurement step, humidity in an analysis space in which the second-environment elution step and the disposition step are performed is measured.

10. The analysis method according to claim 9, wherein the second-environment elution step and the disposition step are performed in the same space.

11. The analysis method according to claim 9, wherein when the second-environment elution step and the disposition step are not performed in the same space, humidity in each space is measured, and an average humidity obtained by proportionally dividing a time from immediately after a start of the second-environment elution step until the second-environment eluate is disposed on the measurement plate is used as the second humidity.

12. The analysis method according to claim 1, wherein in the first humidity measurement step, humidity in an analysis space in which the first-environment elution step is performed is measured.

13. The analysis method according to claim 1, wherein the carrier for the first analysis and the carrier for the second analysis are the same kind of carrier, and the eluate for the first analysis and the eluate for the second analysis are the same kind of eluate.

14. An analysis method comprising:

a humidity measurement step of measuring humidity;

a binding step of bringing a sample containing an analyte into contact with a carrier to bind the analyte to the carrier;

an elution step of bringing the carrier to which the analyte is bound into contact with an eluate containing a volatile organic solvent to elute the analyte into the eluate to obtain an eluate into which the analyte has been eluted, wherein a use amount is used for the eluate;

a disposition step of disposing the eluate into which the analyte has been eluted on a measurement plate for mass spectrometry; and a detection step of detecting the analyte contained in the eluate disposed on the measurement plate by mass spectrometry, wherein the use amount is a sum of a required sample amount to be disposed on the measurement plate, a dead volume, and a volatilization amount of the volatile organic solvent.

15. The analysis method according to claim 1, wherein the second use amount is a sum of a required sample amount to be disposed on the measurement plate, a dead volume, and a volatilization amount of the volatile organic solvent.

* * * * *